United States Patent [19]

Ziemelis

[11] 4,370,160

[45] Jan. 25, 1983

[54] PROCESS FOR PREPARING SILICONE MICROPARTICLES

[75] Inventor: Maris J. Ziemelis, Midland, Mich.

[73] Assignee: Dow Corning Corporation, Midland, Mich.

[21] Appl. No.: 919,588

[22] Filed: Jun. 27, 1978

[51] Int. Cl.$^3$ .................. A01N 37/38; B01J 13/02; B05D 3/06; C08F 30/08

[52] U.S. Cl. .................. 71/117; 71/DIG. 1; 252/316; 252/358; 424/33; 424/94; 424/327; 427/54.1; 524/862

[58] Field of Search .............. 252/316; 424/33, 327; 427/54, 54.1; 71/117; 524/862

[56] References Cited

U.S. PATENT DOCUMENTS

| | | | |
|---|---|---|---|
| 3,257,330 | 6/1966 | Burzynski et al. | 252/316 |
| 3,551,346 | 12/1970 | Breen et al. | 252/316 |
| 3,576,760 | 4/1971 | Gould et al. | 424/33 X |
| 3,726,710 | 4/1973 | Berger et al. | 427/54 X |
| 3,816,282 | 6/1974 | Viventi | 204/159.13 |
| 3,873,499 | 3/1975 | Michael et al. | 260/46.5 E |
| 4,052,529 | 10/1977 | Bokerman et al. | 427/54 X |
| 4,064,027 | 12/1977 | Gant | 204/159.13 |
| 4,118,389 | 10/1978 | Magee | 424/327 X |

FOREIGN PATENT DOCUMENTS

| | | | |
|---|---|---|---|
| 653301 | 12/1962 | Canada | 204/159.13 |
| 52-43779 | 4/1977 | Japan | 252/316 |

*Primary Examiner*—Richard D. Lovering
*Attorney, Agent, or Firm*—George A. Grindahl

[57] ABSTRACT

Microparticles, such as microspheres and microcapsules, comprising a solid organopolysiloxane are prepared by irradiating a dispersion of discrete entities with ultraviolet light. The discrete entities are dispersed in a UV-transparent fluid continuous phase and are sphere-like particles of a UV-curable, liquid organopolysiloxane composition, or such a liquid organopolysiloxane composition containing a material to be encapsulated. The microparticles may be elastomeric or resinous and are useful as filler particles and time-release capsules.

14 Claims, No Drawings

PROCESS FOR PREPARING SILICONE MICROPARTICLES

BACKGROUND OF THE INVENTION

This invention relates to a process for preparing microparticles comprising a solid organopolysiloxane. More particularly, this invention relates to the preparation of microspheres and microcapsules using ultraviolet radiation to convert dispersed discrete entities comprising certain fluid organopolysiloxane compositions to microcapsules and microspheres comprising a solid organopolysiloxane.

Microencapsulation, a means for isolating materials in small containers for subsequent release under controlled conditions, is a relatively new and active art. In the approximately twenty-five years of its commercial life span, however, the microencapsulation art has disclosed only a few methods of making microcapsules, each of which can be conveniently categorized as either a chemical method or a mechanical method. The present invention can be classified as a chemical method of preparing microparticles inasmuch as it comprises crosslinking a liquid organopolysiloxane to the solid state to form the microcapsule.

Organopolysiloxanes have been used in chemical processes for forming microcapsules; however, these methods are very limited in scope. For example, Burzynski et al., U.S. Pat. No. 3,257,330 disclose a process for preparing colored gel particles by hydrolyzing organotrialkoxysilanes in an acidic aqueous medium to form a soluble hydrolyzate and thereafter adding an organic dye and heating the solution until insoluble, hard gel particles containing the dye are formed. This disclosure is limited to a process using heat in an acidic medium and would be of little value for microencapsulating heat-sensitive and/or acid-sensitive materials. Breen et al., U.S. Pat. No. 3,551,346 disclose a process for preparing dual wall capsules. An inner wall is formed by a reaction of a siloxane dissolved in a core material, and an alkaline silanolate, dissolved in an aqueous phase. Subsequently, a non-silicone, outer wall is formed by the well-known coacervation process to provide increased durability to the microcapsule.

Compared to microencapsulation, the preparation of microspheres of solid organopolysiloxane appears to be a non-existent or little-practiced art; however, the method of Burzynski et al., discussed above, would seem to be adaptable for preparing hard gel particles, by merely omitting the dye.

A process for providing microcapsules comprising a durable organopolysiloxane exterior and utilizing neutral, room-temperature conditions is desired for encapsulating acid-, base-, or heat-sensitive material. A process for providing elastomeric or resinous microparticles comprising a solid organopolysiloxane is also desired to provide microparticles of varying strength and utility.

Ultraviolet radiation has only recently been used to form microcapsules. Japanese Pat. No. 52-43779 provides a method for producing microcapsules using a photosensitive resin and ultraviolet radiation. The photosensitive resin comprises a monomer or oligomer having two or more photosensitive groups which will undergo a polymerization reaction under the influence of light energy. Examples of photosensitive groups disclosed therein, which undergo said polymerization reaction, include acryloyl, vinyl ether, vinyl thioether, vinyl ether, vinyl linked to benzene, N,N-vinylalkylamino, allyl, acrylamide, 1,2-alkylene oxide and acetylenyl.

Organopolysiloxane compositions which are curable by ultraviolet light are known from Warrick, Canadian Pat. No. 653,301; Berger et al., U.S. Pat. Nos. 3,726,710; Gant, 4,064,027; Viventi, 3,816,282; Michael et al., 3,873,499; Bokerman et al., 4,052,529 and Gordon et al., U.S. Application No. 856,693, filed on Dec. 2, 1977, now U.S. Pat. No. 4,107,390, issued Aug. 15, 1978, and assigned to the assignee of this invention. These inventions are directed to the preparation of various articles such as silicone rubber, conformed coatings for electronic articles and paper coatings for adhesive release; however, there is no indication that these silicone compositions bearing silicon-bonded olefinic groups may be cured by ultraviolet radiation in the dispersed state or that they may be used to prepare microparticles, such as microspheres and microcapsules.

SUMMARY OF THE INVENTION

It is an object of this invention to provide a new process for preparing microparticles comprising a solid organopolysiloxane.

It is also an object of this invention to provide a process for making microparticles comprising a solid organopolysiloxane under neutral, room-temperature conditions.

It is a further object of this invention to provide a process for preparing microcapsules consisting essentially of an internal material enclosed by a solid organopolysiloxane.

It is another object of this invention to provide a method for preparing microparticles comprising a solid organopolysiloxane which is either elastomeric or resinous.

It is a further object of this invention to provide a method for preparing microcapsules consisting essentially of an internal material which is either dispersed throughout or localized as a core in an enclosing solid organopolysiloxane.

Accomplishment of these and other objects will be obvious upon consideration of the following disclosure and appended claims which in summary, relate to a process for preparing microparticles comprising a solid organopolysiloxane, said process comprising (I) preparing a dispersion consisting essentially of (i) a fluid continuous phase, transparent to ultraviolet radiation and having dispersed therein, (ii) a discontinuous phase consisting essentially of discrete entites comprising a liquid organopolysiloxane composition which is insoluble in the fluid continuous phase and which is convertible to the solid state by ultraviolet radiation under essentially neutral, room-temperature conditions and (II) exposing the dispersion of (I) to ultraviolet radiation until the liquid organopolysiloxane composition is converted to the solid state. The type of microparticle that is produced by this method (microsphere, dispersed microcapsule or core microcapsule) is controlled by the way the dispersion of discrete entities is formed.

DETAILED DESCRIPTION OF THE INVENTION

This invention relates to a process for preparing microspheres of solid organopolysiloxane, said process comprising (I) preparing a dispersion of discrete entities in a fluid continuous phase by dispersing, in the continuous phase fluid, a liquid organopolysiloxane composition convertible by ultraviolet radiation to the solid state, said fluid continuous phase being transparent to ultraviolet radiation and said liquid organopolysiloxane composition being insoluble in the fluid continuous phase and consisting essentially of (a) an organopolysiloxane wherein an average of at least two of the organic radicals per molecule are silicon-bonded olefinic radicals selected from the group consisting of vinyl and butenylene and (b) a hydrogen-containing organopolysiloxane, free of aliphatic unsaturation, wherein the average molecule contains at least two hydrogen radicals selected from the group consisting of silicon-bonded hydrogen and mercaptoalkyl hydrogen, at least one of (a) and (b) having an average of more than two of said olefinic radicals and said hydrogen radicals, respectively, per molecule, and (II) exposing the dispersion of (I) to ultraviolet radiation until the liquid organopolysiloxane composition is converted to the solid state.

This invention also relates to a process for preparing microcapsules consisting essentially of an internal material dispersed throughout a solid organopolysiloxane, said process comprising (I) preparing a dispersion of discrete entities in a fluid continuous phase by dispersing or dissolving the internal material in a liquid organopolysiloxane composition, convertible by ultraviolet radiaton to the solid state, and dispersing the resulting dispersion or solution in the continuous phase fluid, said fluid continuous phase being transparent to ultraviolet radiation and said liquid organopolysiloxane composition being insoluble in the fluid continuous phase and consisting essentially of components (a) and (b) as described above, and (II) exposing the dispersion of (I) to ultraviolet radiation until the liquid organopolysiloxane composition is converted to the solid state.

This invention further relates to a process for preparing microcapsules consisting essentially of an internal material localized as a core in a solid organopolysiloxane, said process comprising (I) preparing a dispersion of discrete entities in a fluid continuous phase by dispersing the internal material in the continuous phase fluid and simultaneously or subsequently codispersing therewith a liquid organopolysiloxane composition, said fluid continuous phase being transparent to ultraviolet radiation and said liquid organopolysiloxane composition being insoluble in the fluid continuous phase and consisting essentially of components (a) and (b) as described above, and (II) exposing the dispersion of (I) to ultraviolet radiation until the liquid organopolysiloxane composition is converted to the solid state.

Microparticles, as used herein, in a generic term and includes microspheres and microcapsules comprising a solid organopolysiloxane. Microspheres, as used herein, are homogeneous microparticles consisting essentially of organopolysiloxane, at least the exterior of which is solid. Microcapsules, as used herein, are homogeneous or heterogeneous microparticles consisting essentially of an internal material which is different from and surrounded by the solid organopolysiloxane. Microcapsules may contain the internal i.e. encapsulated, material dispersed throughout, or localized as a core in, the solid organopolysiloxane.

Microparticles, for the purposes of this invention, are essentially sphere-like particles having a diameter of up to about 5 mm, but preferably from 0.005 to 1 mm. Microcapsules having a relatively large solid core may deviate from a sphere-like shape to the extent that the shape of the solid core deviates from a sphere-like shape. It is to be understood that the method of this invention provides predominantly discrete microparticles; however, small amounts of aggregated microparticles, held together by physical and/or chemical bonding, may also be prepared thereby.

Ultraviolet radiation (UV), as used herein, is electromagnetic radiation having one or more wavelengths between 200 and 400 nm.

Liquid organopolysiloxane compositions convertible by ultraviolet radiation to the solid state (herein also labeled the convertible organopolysiloxane composition) which are suitably operative in the process of this invention must experience a change to the solid, i.e. non-flowing, state when exposed to ultraviolet radiation. Compositions meeting this requirement comprise a liquid homogeneous mixture of two types of organopolysiloxanes; (a) an organopolysiloxane bearing an average of at least two reactive olefinic radicals per molecule and (b) an organopolysiloxane bearing an average of at least two reactive hydrogen radicals per molecule. In addition, at least one of said organopolysiloxanes has an average of more than two, preferably three or more, of said reactive radicals per molecule. Preferably both component (a) and component (b) have an average of three or more of said reactive olefinic radicals and reactive hydrogen radicals, respectively, per molecule.

Reactive olefinic radicals include the silicon-bonded vinyl radical and the butenylene radical, divalently bonded to one silicon atom. Butenylene includes —CH$_2$CH=CHCH$_2$— and —CH=CHCH$_2$CH$_2$— radicals bonded to silicon as follows:

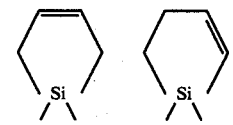

The group comprising the butenylene radical divalently bonded to one silicon atom, and depicted above, is designated the silacyclopentene group.

Reactive hydrogen radicals include the silicon-bonded hydrogen radical and the alkylmercapto-bonded hydrogen radical, as it occurs in a radical of the formula —C$_n$H$_{2n}$SH. The value of n may be an integer from 1 to 6, giving rise to mercaptoalkyl radicals such as mercaptomethyl, 2-mercaptoethyl, 3-mercaptopropyl, 3-mercaptobutyl and 4-mercaptobutyl.

Organopolysiloxanes (a) and (b) each consist of a plurality of siloxane units of the general formula R$_a$SiO$_{(4-a)/2}$ wherein a is an integer less than 4 and represents the number of silicon valences bonded to R radicals. The value of a is equal to the number of R radicals bonded to the silicon atom when all R radicals are monovalently bonded thereto and is equal to one plus the number of R radicals bonded to the silicon atom when the silicon atom bears a butenylene radical.

Herein, R denotes an organic radical having from 1 to 6 carbon atoms selected from the group consisting of alkyl radicals, such as methyl, ethyl, propyl and isopropyl; cycloaliphatic radicals, such as cyclopentyl and cyclohexyl; haloalkyl radicals, such as 3-chloropropyl and 3,3,3-trifluoropropyl; haloaromatic radicals, such as 2,4-dichlorophenyl; and a reactive radical selected from the group consisting of vinyl, butenylene, hydrogen and mercaptoalkyl, as delineated above. No organopolysiloxane molecule bears both reactive olefinic radicals and reactive hydrogen radicals. Preferably no siloxane unit of the organopolysiloxanes bears more than one of said reactive radicals.

Organopolysiloxanes (a) and (b) may be composed of any combination of siloxane units of the formulae $R_3SiO_{1/2}$, $R_2SiO_{2/2}$, $RSiO_{3/2}$, and $SiO_{4/2}$, bonded together by Si-O-Si bonds, provided that their mixture to form the convertible organopolysiloxane composition results in a liquid at room temperature. Preferably, both component (a) and component (b) are liquids at room temperature.

Examples of suitable siloxane units for either component (a) or (b) are endblocking triorganosiloxane units, such as $Me_3SiO_{1/2}$, $PhMe_2SiO_{1/2}$, $EtMe_2SiO_{1/2}$, $C_6H_{11}Me_2SiO_{1/2}$, $CF_3CH_2CH_2Me_2SiO_{1/2}$, $C_6H_3Cl_2Me_2SiO_{1/2}$, $i\text{-}PrMe_2SiO_{1/2}$, $PhEtMeSiO_{1/2}$ and $Ph_2MeSiO_{1/2}$; backbone diorganosiloxane units, such as $Me_2SiO_{2/2}$, $PhMeSiO_{2/2}$, $CF_3CH_2CH_2MeSiO_{2/2}$, $Ph_2SiO_{2/2}$, $ClCH_2CH_2CH_2MeSiO_{2/2}$ and $C_6H_{11}MeSiO_{2/2}$; and branching monoorganosiloxane units, such as $MeSiO_{3/2}$, $PhSiO_{3/2}$, $EtSiO_{3/2}$, $CF_3CH_2CH_2SiO_{3/2}$, $ClCH_2CH_2CH_2SiO_{3/2}$ and $C_6H_{11}SiO_{3/2}$ and $SiO_{4/2}$.

Examples of suitable siloxane units bearing reactive olefinic radicals for component (a) include $Me_2ViSiO_{1/2}$, $PhMeViSiO_{1/2}$, $CF_3CH_2CH_2MeViSiO_{1/2}$, $MeBtSiO_{1/2}$, $MeViSiO_{2/2}$, $PhViSiO_{2/2}$, $CF_3CH_2CH_2ViSiO_{2/2}$, $BtSiO_{2/2}$ and $ViSiO_{3/2}$ wherein Bt denotes the butenylene radical.

Examples of suitable siloxane units bearing silicon-bonded hydrogen radicals for component (b) include $HMe_2SiO_{1/2}$, $HPhMeSiO_{1/2}$, $HMeCF_3CH_2CH_2SiO_{1/2}$, $HMeSiO_{2/2}$, $HPhSiO_{2/2}$, $HCF_2CH_2CH_2SiO_{2/2}$ and $HSiO_{3/2}$.

Examples of suitable siloxane units bearing alkylmercapto-bonded hydrogen radicals for compoent (b) include $HSCH_2CH_2CH_2Me_2SiO_{1/2}$, $HSCH_2CH_2CH_2MeSiO_{2/2}$ and $HSCH_2CH_2CH_2SiO_{3/2}$.

Herein Me, Et, i-Pr, Ph, Vi and $C_6H_{11}$ denote the methyl ethyl, isopropyl, phenyl, vinyl and cyclohexyl radical, respectively.

It is also within the scope and spirit of this invention to allow, in components (a) and (b), small amounts of non-essential radicals such as silicon-bonded hydroxy, methoxy, ethoxy and isopropoxy radicals. These radicals are usually bonded to endblocking siloxane units by design or are present on any siloxane unit as a residual radical arising from the particular process that was used to prepare the component. Preferably components (a) and (b) are free of said non-essential radicals.

Organopolysiloxanes (a) and (b) may be prepared by any suitable method. Generally, hydrolyzable organosilanes of the general formula $R_aSiX_{4-a}$ may be combined in the proper amounts and hydrolyzed to form a hydrolyzate which is equilibrated using an acidic or alkaline catalyst. Herein a is as denoted above and X denotes a hydrolyzable radical such as halogen radical such as chloro or bromo, an alkoxy radical such as methoxy or ethoxy, an acyloxy radical such as acetoxy or a silicon-nitrogen-bonded radical such as methylethylketoximo, dimethylamino or N-methylacetamido. Polydiorganosiloxanes are also conveniently prepared by catalytic ring-opening of cyclopolydiorganosiloxanes in the well-known manner.

Specific methods for preparing organopolysiloxanes bearing silicon-bonded vinyl radicals or silicon-bonded hydrogen radicals are well-known in the art and need no further documentation herein.

Specific methods for preparing organopolysiloxanes bearing silicon-bonded mercaptoalkyl radicals may be found in U.S. Pat. Nos. 3,632,715; 3,873,499; 4,046,795; 4,052,529 and 4,064,027 the disclosures of which are hereby incorporated herein by reference to show the preparation of some suitable mercaptoalkyl-containing organopolysiloxane.

Specific methods for preparing organopolysiloxanes bearing silicon-bonded butenylene radicals may be found in U.S. Pat. No. 3,509,191, the disclosure of which is hereby incorporated herein by reference to show the preparation of some suitable butenylene-containing organopolysiloxanes.

The convertible organopolysiloxane compositions preferably contain a photosensitizer to decrease the time that is needed to convert the organopolysiloxane composition from the liquid to the solid sate, under the influence of ultraviolet radiation. Photosensitizers are well known in the art and include, for example, acetophenone, benzophenone, propiophenone, xanthone, anthraquinone, fluorenone, 3-methylacetophenone, 3-bromoacetophenone, 4-methylbenzophenone, benzaldehyde, carbazole and triphenylamine. The amount of any particular photosensitizer to be used in this invention is merely an amount sufficient to photosensitize the system, as indicated by an improved rate of microparticle formation. Generally, an amount of up to 5 percent by weight of photosensitizer, based on the total amount of components (a) and (b), is sufficient.

The convertible organopolysiloxane compositions are liquid at room temperature, i.e. they flow. The viscosity of the liquid mixture is not critical and may range from a few millipascal-seconds up to 100 pascal-seconds at 25° C. A preferred viscosity of the convertible organopolysiloxane composition to be used for any particular combination of internal material and fluid continuous phase may be determined by routine experimentation.

Generally, elastomeric microparticles are obtained from convertible organopolysiloxane compositions wherein component (a) and component (b) are free of $RSiO_{3/2}$ and $SiO_{4/2}$ siloxane units and the total of all reactive radicals in (a) plus (b) does not exceed 10 percent of all the R radicals therein. As the number of $RSiO_{3/2}$ and $SiO_{4/2}$ siloxane units and/or the percentage of reactive radicals therein are increased more-resinous microparticles are obtained.

In one embodiment of this invention the convertible organopolysiloxane composition consists essentially of a mixture of (a) an organopolysiloxane selected from the group consisting of cyclopolymethylvinylsiloxanes having from 3 to 10 silicon atoms and 1,1'-oxy-bis(1-methyl-1-silacyclopentene), (b) a triorganosiloxane-endblocked polydiorganosiloxane fluid having a viscosity of from 0.5 to 50 pascal-seconds at 25° C. and containing up to 10 mol percent of methyl-3-mercaptopropylsiloxane units and at least 90 mol percent dimethylsiloxane units and (c) a photosensitizing amount of benzophenone, the amounts of (a) and (b) being sufficient to provide a mol ratio of mercaptopropyl radicals to olefinic radicals of from 0.5 to 5.0. This convertible organopolysiloxane composition provides microparticles comprising an elastomeric organopolysiloxane.

In another embodiment of this invention the convertible organopolysiloxane composition consists essentially of (a) a triorganosiloxane-endblocked polydiorganosiloxane fluid having a viscosity of from 0.5 to 50 pascalseconds at 25° C. and containing up to 10 mol percent methylvinylsiloxane units and at least 90 mol percent dimethylsiloxane units, (b) a triorganosiloxane-endblocked polymethylhydrogensiloxane having approximately 35 silicon atoms and (c) a photosensitizing amount of benzophenone, the amounts of (a) and (b) being sufficient to provide a mol ratio of silicon-bonded hydrogen radicals to silicon-bonded vinyl radicals of from 1.0 to 10.0. This convertible organopolysiloxane composition provides microparticles comprising an elastomeric organopolysiloxane which is free of sulfur atoms.

Examples of UV-curable organopolysiloxane compositions that are suitable for use in this invention as the convertible organopolysiloxane composition may be found in U.S. Pat. Nos. 3,873,499; 4,052,529; 4,064,027 and allowed U.S. Application No. 856,693, now U.S. Pat. No. 4,107,390, issued Aug. 15, 1978, the disclosures of which are incorporated herein to show the preparation of suitable convertible organopolysiloxane compositions.

The internal material, i.e. the material to be encapsulated by the process of this invention, may be any solid of suitable particle size not exceeding 5 mm in diameter, liquid or gas which does not chemically react with the fluid continuous phase or the convertible organopolysiloxane compositon or which does not dissolve extensively in the fluid continuous phase. Obviously, the internal material should not be adversely affected by the ultraviolet radiation that is used in the process of this invention.

Examples of suitable internal materials for this invention include adhesives, catalysts, colorants, cosmetics, curing agents, deodorants, detergents, drugs, enzymes, flavors, foods, fuels, inks, insecticides, metals, medicaments, monomers, odorants, oils, pheromones, plasticizers, propellants, solvents, solid substrates containing an adsorbed active component and vitamins.

When microencapsulating solid materials it is preferred to reduce the material to the desired particle size before preparing the dispersion to be irradiated. Liquid internal materials need no special treatment. Gaseous materials are best microencapsulated using the method for preparing discrete entities comprising dispersing the gas in the liquid organopolysiloxane compositions, as a first step.

The fluid continuous phase, suitable for use in the method of this invention, must be at least partially transparent to one or more wavelengths of ultraviolet radiation that are operative to convert the convertible organopolysiloxane composition to the solid state. Preferably the fluid continuous phase should be essentially completely transparent to said operative wavelengths and most preferably to the entire spectrum from 200 to 400 nm.

The fluid continuous phase must be chemically unreactive with and not dissolve the convertible organopolysiloxane composition. Although it is not necessary, especially when preparing microcapsules having a dispersed internal material, it is preferred that the fluid continuous phase will not dissolve the internal material extensively.

The fluid continuous phase may be a gas, but preferably it is a liquid of suitable viscosity to permit the forming and maintaining of the dispersion.

Examples of fluids that are suitable for use as the continuous phase in the method of this invention are air, nitrogen, steam, water, mineral oil, and perfluorocarbons. Selection of a suitable match of internal material and fluid continuous phase should be made to satisfy the non-reactivity and non-solubility requirements noted above.

In a preferred embodiment of this invention the fluid continuous phase is water which contains a dispersion-stabilizing amount of a surfactant of the oil-in-water type to aid in the formation of the dispersion and to minimize agglomeration of discrete entities and microparticles during the irradiation process. Said surfactant may be of the anionic type, such as salts of alkyl sulfates, salts of alkyl benzene sulfonates and salts of poly(oxyethylene)sulfates; the cationic type, such as quaternary ammonium salts with long chain alkyl groups and pyridinium salts; or the non-ionic type, such as poly(oxyethylene)alkyl ethers, poly(oxyethylene)alkylphenol ethers, and poly(oxyethylene)alkyl esters. Preferably any surfactant that is used is free of aliphatic unsaturation to preclude its reacting with the convertible organopolysiloxane composition during irradiation. The proper amount of oil-in-water type surfactant to be used may vary widely and can be determined by simple experimentation. Generally, less than 5 percent by weight, based on the weight of water, is sufficient.

In the method of this invention a dispersion consisting essentially of discrete entities, hereinafter further delineated, dispersed in a UV-transparent fluid continuous phase, is prepared and is simultaneously or subsequently exposed to ultraviolet radiation to convert the discrete entities to microparticles. Said dispersion may be prepared by any suitable method, such as stirring, homogenizing and emulsifying, which will provide a discontinuous phase of discrete entities which are maintained in the dispersed state while the dispersion is being exposed to ultraviolet radiation.

In one embodiment of this invention, which provides microspheres, the discrete entities consist essentially of spheres, up to about 5 mm in diameter, of a liquid organopolysiloxane composition which is convertible to the solid state by ultraviolet radiation. These discrete entities may be prepared by dispersing the liquid organopolysiloxane composition in the continuous phase fluid using any suitable method for dispersing a liquid in an incompatible fluid. These methods are well known in the art and need not be detailed here. On exposure to ultraviolet radiation these discrete entities experience a curing reaction which converts at least the exterior surface thereof to the solid state to provide microspheres. Optionally, the discrete entities may be exposed to ultraviolet radiation for a sufficient period of time to completely convert them to solid microspheres. These microspheres, either elastomeric or resinous, are useful as filler particles in various fluid compositions such as greases, sealants and adhesives and as substrate particles in chromatography columns.

In another embodiment of this invention, which provides microcapsules, the discrete entities consist essentially of sphere-like particles, up to about 5 mm in diameter, having an internal material surrounded by a convertible organopolysiloxane composition. On exposure to ultraviolet radiation the convertible organopolysiloxane composition is converted to the solid state thereby encapsulating the internal material and providing microcapsules. These microcapsules are useful as time release capsules, such as for the controlled release of herbicides, fertilizers and medicaments. However, the type of microcapsules that are produced by the method of this invention is determined by the manner in which the dispersion to be irradiated is prepared.

In a first manner for preparing the dispersion of discrete entities consisting essentially of an internal material surrounded by a convertible organopolysiloxane composition the internal material to be microencapsulated is first dissolved or dispersed in the convertible organopolysiloxane composition and the resulting solution or dispersion is thereafter dispersed in the continuous phase fluid. In this manner a major portion of microcapsules containing the internal material dissolved and/or dispersed throughout the solid organopolysiloxane is obtained after irradiation. When the internal material is insoluble in the liquid organopolysiloxane composition, there also may be obtained minor amounts of microcapsules containing a discrete core of internal material. To provide a maximum portion of microcapsules having a dispersed internal material, vigorous mixing of the internal material and the convertible organopolysiloxane composition should be used. In some cases it may be desired or necessary to use a suitable surfactant to achieve proper dispersion of an internal material which is insoluble in the convertible organopolysiloxane composition.

In a second manner for preparing the dispersion of discrete entities consisting essentially of an internal material surrounded by a convertible organopolysiloxane composition the internal material to be encapsulated is dispersed in the continuous phase fluid and the convertible organopolysiloxane composition is simultaneously, or subsequently, codispersed therewith. In this manner a major portion of microcapsules containing the internal material localized as a discrete core in the solid organopolysiloxane is obtained after irradiation. There also may be obtained by this second manner minor amounts of microspheres of solid organopolysiloxane which are free of the internal material. For maximum yield of microcapsules having a discrete core of internal material it is preferred to disperse the internal material and the convertible organopolysiloxane composition simultaneously in the fluid continuous phase, using moderate mixing such as stirring, rather than homogenizing or emulsifying.

The dispersion of discrete entities in fluid continuous phase may be exposed to ultraviolet radiation at any suitable time. Preferably the dispersion is exposed to ultraviolet radiation as soon as it is formed and the exposure is continued until the convertible organopolysiloxane composition is converted to the desired state of solidification. In the case of shelf-stable dispersions exposure thereof to ultraviolet radiation may be delayed, if desired.

The dispersion of discrete entities in fluid continuous phase may be irradiated in any of the well-known manners such as by immersion of an electrically protected ultraviolet radiation source in the dispersion or by external exposure of the dispersion to a suitable source such as a mercury vapor lamp, an electric arc or the sun. Of course, the rate of conversion of discrete entities to microparticles is directly related to the intensity of ultraviolet radiation incident on the convertible organopolysiloxane composition and one should consider exposure parameters, such as the intensity of the ultraviolet source, its distance from the dispersion and the nature of the intervening space, when practicing the method of this invention.

It is also known that silicon-bonded hydrogen radicals are readily reactive with ultraviolet radiation having a wavelength of less than 365 nm. Ultraviolet radiation having a wavelength of 254 nm is most effective with sulfur-bonded hydrogen radicals.

The dispersion of discrete entities in fluid continuous phase is exposed to ultraviolet radiation until the desired degree of solidification of the convertible organopolysiloxane composition has been achieved. This is conveniently determined by visual inspection. In a preferred method, aliquots of the exposed dispersion are periodically taken and examined under magnification. The dispersion is exposed to ultraviolet radiation at least until the convertible organopolysiloxane is non-flowing. This is conveniently determined by placing the microparticles on a microscope slide and ascertaining the absence of organopolysiloxane film formation on the slide. Preferably the dispersion is exposed until the microparticles have sufficient strength to permit isolation by standard methods such as filtration and centrifugation without fragmenting the solid organopolysiloxane. Further curing may be done, if desired.

In the method of this invention the microparticles may be separated from or allowed to remain in the reaction mixture after irradiation, as desired. However, because of the pervious nature of organopolysiloxane elastomers and resins, microcapsules containing an internal material which is soluble in the fluid continuous phase should be separated from the fluid continuous phase as soon as they are formed or shortly thereafter to minimize any undesired leaching of the internal material by the fluid continuous phase.

It is believed that the best way to practice the present invention is detailed in the following examples which are presented to further illustrate, but not to limit the invention which is properly delineated by the appended claims.

All parts and percentages are by weight unless otherwise specified. Viscosities were measured in centipoise at 25° C. and were converted to pascal-seconds for this application by multiplying by 0.001 and rounding off. Pressure was measured in torr and was converted to pascals by multiplying by 133.322 and rounding off.

The source of ultraviolet radiation was a 100 W Hanovia medium pressure mercury vapor lamp having ultraviolet emissions at 180, 185, 238, 248, 254, 265, 280, 297, 302, 313 and 366 nm.

EXAMPLE 1

This example shows the microencapsulation of a discrete core of mineral oil.

A mercaptopropyl-containing polydiorganosiloxane was prepared by heating, for 6 hours at 70° C., a mixture of 446 parts of cyclopolydimethylsilxoanes, 3.95 parts of hexamethyldisiloxane, 42.5 parts of cyclopolymethylmercaptopropylsiloxane and 0.25 parts of $CF_3SO_3H$. The rection mixture was thereafter stirred with 2.5 parts of $Na_2CO_3$ and 2.5 parts of ground perlite and filtered. The clear filtrate was devolatilized at 150° C. and 4 torr (533 Pa) pressure to give 420 parts of a trimethylsiloxane-endblocked polydiorganosiloxane fluid having a viscosity of 1.18 Pa.s., a sulfhydryl content of 2.27 percent and a refractive index of 1.4112. The fluid had approximately 240 dimethylsiloxane units and approximately 13 methyl-3-mercaptopropylsiloxane units per average molecule and an average of two monovalent radicals per silicon atom.

A homogeneous, liquid organopolysiloxane composition, convertible to the solid state by ultraviolet radiation, was prepared by mixing 95.5 parts of the above polydiorganosiloxane fluid, 3.0 parts of cyclopolymethylvinylsiloxane of the formula {CH$_3$(CH$_2$=CH)SiO}$_{4-6}$ and 1.5 parts of benzophenone. This composition was used in Examples 1 to 8 to prepare elastomeric microcapsules and microspheres.

A quartz test tube, 76 mm×280 mm, fitted with a stopper bearing a thermometer, an addition funnel and a paddle stirrer was charged with 90.0 g. of mineral oil as the internal material to be microencapsulated, 400 g. of water as the fluid continuous phase and 10.0 g. of the homogeneous, convertible mixture described above. The paddle stirrer was rotated at 700 r.p.m. and 0.05 g. of octylphenoxypolyethoxy(40)ethanol (Triton ® X-405) was added to the mixture to aid in preparing a dispersion. While being stirred at 700 r.p.m. the resulting dispersion of discrete entities was irradiated for 30 minutes with ultraviolet light from a 100 W medium pressure mercury vapor lamp placed 10 mm from the test tube. The reaction mixture was then filtered and the microcapsules were washed twice with distilled water and allowed to dry in the air; 76 g. of microcapsules was obtained. Several of the microcapsules were examined at 50x magnification, before and after mechanical rupturing, and were found to consist of spherical shells of elastomeric material containing a discrete nucleus of mineral oil. Several microcapsules having a diameter of 880 $\mu$m. were found to have uniform wall thicknesses ranging from 22 to 66 $\mu$m.

EXAMPLE 2

This example shows the microencapsulation of a dispersed polydimethylsiloxane oil.

As an internal material 33 g. of a trimethylsiloxane-endblocked polydimethylsiloxane oil having a viscosity of 1.0 Pa.s was dissolved in 100 g. of the homogeneous convertible mixture of Example 1 and the solution was thereafter slowly added to a stirred solution of 6.0 g. of octylphenoxypolyethoxy(10)ethanol (Triton ® X-100) in 394 g. of water. The resulting dispersion was irradiated and stirred for 30 minutes using the apparatus described in Example 1, after which the resulting microcapsules were filtered, washed with water and dried to provide soft waxy spherical capsules approximately 1 mm in diameter and containing encapsulated polydimethylsiloxane oil dispersed throughout the microcapsules.

EXAMPLE 3

This example shows the microencapsulation of a commercial antifoam.

Example 2 was repeated except that 33 g. of a commercial antifoam, sold as Dow Corning ® Antifoam "A", was used in place of the polydimethylsiloxane oil as the internal material. Irradiation was conducted at 24° C. for 15 minutes and at a slower stirring rate, compared to that in Example 1, to give larger microcapsules having an average diameter of 4 to 5 mm and containing the antifoam preparation dispersed throughout the microcapsules.

EXAMPLE 4

This example shows the microencapsulation of air.

Fifty grams of the homogeneous, convertible mixture of Example 1 was vigorously mixed with 1 g. of octylphenoxypolyethoxy(10)ethanol using an Eppenbach mixer and allowing air to be entrapped in the mixture. The resulting mixture was added to 394 g. of water containing 6 g. of octylphenoxypolyethoxy(10)ethanol as in Example 1. After 20 minutes of irradiation and stirring in the quartz reaction apparatus of Example 1 the reaction mixture was washed and dried to provide microcapsules having diameters ranging from 1 to 3 mm. Microscopic examination of these capsules showed encapsulated air bubbles, up to 0.1 mm in size, within the microcapsules.

EXAMPLE 5

This example shows the microencapsulation of a dispersed solid insecticide.

Fifteen grams of the homogeneous, convertible mixture of Example 1 was mixed with 35 g. of 3,3-dimethyl-1-(methylthio)-2-butanone-O-{(methylamino)carbonyl}oxime, known generally as thifanox. The mixture was then vigorously mixed in an Eppenbach mixer to provide a white creamy fluid which was dispersed in 395 g. of water containing 5 g. of octylphenoxypolyethoxy(10)ethanol using the quartz reaction apparatus described in Example 1. The dispersion of discrete entities was stirred at 600 r.p.m. and irradiated for 30 minutes, after which the microcapsules were filtered, washed 4 times with distilled water and dried in a vacuum desiccator. The microcapsules, 0.5 to 1.0 mm in diameter, were found by microscopic examination under polarized light to contain the crystalline insecticide dispersed throughout the microcapsule.

Smaller microcapsules, ranging in size from 0.01 to 0.1 mm and containing dispersed insecticide, were prepared as described above except that the insecticide was ground to a fine powder first and then dispersed in the homogeneous, convertible organopolysiloxane mixture and the resulting white creamy fluid was emulsified in 100 g. of water containing 1 g. of octylphenoxypolyethoxy(10)ethanol using an Eppenbach mixer. The resulting emulsion was then dispersed in water and surfactant as before and irradiated for 35 minutes while being stirred. Filtering, washing and drying of the product provided 37.2 g. of the smaller microcapsules.

EXAMPLE 6

This example shows the microencapsulation of a dispersed solid herbicide in microcapsules having proportions of solid organopolysiloxane.

Six grams of the homogeneous, convertible mixture of Example 1 and 14 g. of 2,4-dichlorophenoxyacetic acid (2,4-D) were mixed for 15 minutes using a mechanical shaker. The resulting mixture was ground in a mortar and pestle to a sticky white paste which was then dispersed in 600 g. of water containing 6 g. of octylphenoxypolyethoxy(10)ethanol, using the quartz reaction tube of Example 1. The resulting dispersion was stirred at 500 r.p.m. and irradiated for 30 minutes during which time the temperature of the dispersion rose from 20° to 23° C. The resulting microcapsules, 1 to 5 mm in diameter, were filtered, washed and dried and weighed (16.5 g). The microcapsules contained 10.8 percent silicon whereas the homogeneous convertible organopolysiloxane composition alone contained 35.5 percent silicon, thereby showing that the microcapsules contained 30.4 percent (expected, 30 percent) of the organopolysiloxane composition.

This example was repeated, except that 18 g. of 2,4-D and 2.0 g. of the homogeneous, convertible organopolysiloxane composition were used. Microscopic examination of the dried microcapsules, 17.1 g., showed them to be 1 mm aggregates of smaller microcapsules ranging in size from 0.1 to 0.2 mm. A silicon content of 3.1 percent showed the microcapsules to be 8.7 percent (expected, 10 percent) organopolysiloxane composition.

This example was repeated again, except that 19.8 g. of 2,4-D and 0.2 g. of the homogeneous, convertible organopolysiloxane composition was used. Microscopic examination of the dried microcapsules, 16.7 g. showed them to be individual microcapsules ranging in size from 0.05 to 0.1 mm. These microcapsules were expected to contain 1 percent organopoly-siloxane which placed the silicon content below the limits of the analytical method. However, extraction of these microcapsules with acetone removed the encapsulated 2,4-D, and left swollen shells of elastomeric material.

A sample of each of the above-prepared microcapsules was placed in water to provide a potential 812 mg. of 2,4-D per liter of water. Untreated 2,4-D was also placed in water at the same concentration. Samples of the water phase of each of the four mixtures were periodically taken and analyzed spectrophotometrically to determine the concentration of dissolved 2,4-D in the water. In six hours approximately 67 percent of the untreated 2,4-D and 67 percent of the 2,4-D microencapsulated with 1 percent organopolysilxoane had dissolved, while only 48 percent and 19 percent of the 2,4-D which had been microencapsulated with 8.7 percent and 30.4 percent, respectively, of organopolysiloxane had entered the water. This demonstrates the utility of the microcapsules, made by the method of this invention, as time release microcapsules.

EXAMPLE 7

This example shows the microencapsulation of a dispersed enzyme.

Fifty grams of the homogeneous, convertible compositions of Example 1 was mixed with 10.0 g. of urease (Matheson, Coleman and Bell UX-80) using an Eppenbach mixer. A mixture of 394 g. of water and 6 g. of octylphenoxypolyethoxy(10)ethanol was placed in the quartz test tube described in Example 1 and stirred. Ultraviolet irradiation of the tube contents was started and the urease-containing mixture was dispersed into the irradiated, stirred water phase. The stirred dispersion was irradiated for 17 minutes and the resulting microcapsules were then filtered, washed with three portions of distilled water and dried to provide 38 g. of light yellow microcapsules ranging from 0.3 to 1.0 mm in diameter. Nitrogen content of the urease and of the microcapsules was found to be 6.1 percent and 0.6 percent, respectively, thereby showing that the microcapsules contained 9.8 percent urease, versus a theoretical content of 20 percent. The missing urease was probably dissolved in the continuous water phase.

Approximately 7 g. of the microcapsules were placed in a 50 ml. analytical buret and distilled water was passed through the buret under gravity feed at a rate of from 0.8 to 2.0 ml./min. After eluent volumes of 2045, 3965 and 8650 ml., the microcapsules were sampled and were found to contain 0.48, 0.40 and 0.36 percent nitrogen, respectively, indicating that 60 percent of the urease in the microcapsules was not extractable.

The microcapsules containing 0.36 percent nitrogen were then mixed with an enzyme-activity test solution consisting of 25 g. of urea, 475 g. of water and 5 ml. of 1 percent phenophthalein in ethanol. This test solution turns pink when mixed with urease due to the enzymatic formation of ammonia. The mixture of microcapsules containing urease and the enzyme-activity test solution turned pink in a few minutes, showing that the microencapsulated urease is active, although immobilized.

EXAMPLE 8

This example shows the conversion of liquid organopolysiloxane to microspheres consisting only of solid elastomeric organopolysiloxane.

One hundred grams of the liquid convertible organopolysiloxane composition of Example 1 was dispersed in 394 g. of water containing 6 g. of octylphenoxypolyethoxy(10)ethanol using the quartz reaction vessel of Example 1. A sample of the dispersion was taken immediately. After 5 minutes of stirring the ultraviolet radiation was started. After 5 and 10 minutes of irradiation samples of the irradiated dispersion were taken. After 13 minutes of irradiation the ultraviolet radiation and the stirring were stopped and the product was filtered, washed with water and dried. Microscopic examination of the final microspheres revealed a distribution of microcapsules ranging from 0.1 to 1.0 mm in diameter. The samples taken at the beginning and after 5 and 10 minutes of irradiation were each spread into a film and allowed to dry. The beginning sample yielded an oily organopolysiloxane film whereas the other samples yielded solid microspheres, thereby showing that only five minutes of irradiation was needed to convert the liquid organopolysiloxane to the solid state.

EXAMPLE 9

This example shows the microencapsulation of a solid herbicide dispersed throughout a resinous organopolysiloxane solid.

A mixture of 4 molar parts of $HSCH_2CH_2CH_2Si(OCH_3)_3$, 11 molar parts of $(CH_3)_2CHCH_2CH_2SiCl_3$, 4 molar parts of $(CH_3)_2SiCl_2$ and 1 molar part of $(CH_3)_3SiCl$ was added over a period of 10 minutes to a stirred mixture of 61.2 molar parts of water and 4.1 molar parts of toluene. The resulting mixture was heated at 60° C. for 15 minutes, the oily layer was separated from the aqueous layer and the oily layer was washed with 10 percent aqueous NaCl. The oily layer was then refluxed for 1 hour at 109° C. and 0.13 molar parts of water was removed by way of the toluene-water azeotrope. p-Toluenesulfonic acid, 0.004 molar parts, was then added to the refluxing oily material and an additional 0.1 molar parts of water was similarly removed during 2.5 hours of refluxing. The reaction product was cooled to 25° C., mixed with 0.03 molar parts of $(CH_3)_3SiNHSi(CH_3)_3$ for 30 minutes and devolatilized at 139° C. and 9 torr (1.2 kPa) pressure to yield a hazy fluid. Fresh toluene was added to the hazy fluid and the solution was filtered. Devolatilization of the filtrate at 140° C. and 1.3 kPa pressure yielded a fluid having a viscosity of 6.8 Pa.s and a sulfhydryl content of 5.77 percent (theory, 5.90 percent).

A homogeneous, liquid organopolysiloxane composition, convertible to the solid state by ultraviolet radiation, was prepared by mixing 25.6 parts of the above mercaptopropyl-containing organopolysiloxane fluid, 1.9 parts of cyclopolymethylvinylsiloxane of the formula $\{CH_3(CH_2=CH)SiO\}_{4-6}$ and 0.5 parts of benzophenone.

Twelve grams of 2,4-D was dispersed in 28 g. of the above homogeneous, convertible composition using a spatula and the resulting dispersion was dispersed in 200 g. of water containing 1 g. of octylphenoxypolyethoxy(10)ethanol, using the quartz reaction tube of Example 1. The dispersion was stirred and irradiated for 30 minutes after which the microcapsules were filtered, washed 5 times with 100 ml. portions of water and dried. The microcapsules, having diameters of from 0.1 to 0.3 mm and containing dispersed 2,4-D, weighed 26.2 g. and contained 9.6 percent chlorine and 16.8 percent silicon. The mixture of convertible composition and 2,4-D had a theoretical analysis of 9.6 percent chlorine and 17.4 percent silicon, showing that the microcapsules have essentially the same composition as the irradiated entities.

EXAMPLE 10

This example shows the preparation of microspheres consisting only of solid resinous organopolysiloxane.

Fifty grams of the homogeneous, convertible compositions of Example 9 was dispersed in 400 g. of water containing 4 g. of octylphenoxypolyethoxy(10)ethanol, as in Example 9, and irradiated for 15 minutes. The resulting product was filtered, washed and dried to give 43.1 g. of microspheres ranging in size from 0.1 to 0.3 mm. These microspheres were harder than the microspheres produced in Examples 8, 11 and 13.

EXAMPLE 11

This example shows the preparation of microspheres from a liquid organopolysiloxane composition wherein the olefin component bears only two olefinic radicals per molecule.

A homogeneous, liquid organopolysiloxane composition, convertible to the solid state by ultraviolet radiation, was prepared by mixing 47.72 parts of the mercaptoalkyl-containing polydiorganosiloxane having a viscosity of 1.18 Pa.s and described in Example 1, 1.53 parts of 1,1'-oxy-bis(1-methyl-1-silacyclopentene) and 0.75 parts of benzophenone.

Fifty grams of the above composition was dispersed and irradiated as in Example 10 except that irradiation was continued for 60 minutes, 15 and 30 minutes being insufficient to convert the liquid organopolysiloxane composition to the solid state. The resulting microspheres ranged in size from 0.2 to 0.3 mm.

EXAMPLE 12

This example shows the microencapsulation of dispersed aspirin in a sulfur-free organopolysiloxane.

A trimethylsiloxane-endblocked polydiorganosiloxane fluid having a viscosity of 1.22 Pa.s and a vinyl content of 3.42 percent and consisting of 90 mol percent dimethylsiloxane units and 10 mol percent methylvinylsiloxane units was prepared by equilibrating 11.72 molar parts of cyclopolydimethylsiloxanes, 1.32 molar parts of cyclopolymethylvinylsiloxanes and 0.04 molar parts of dodecylmethylpentasiloxane using an alkaline catalyst in the well-known manner. The alkaline catalyst was thereafter neutralized with 0.0014 molar parts of trimethylchlorosilane and the resulting fluid was filtered and devolatilized at 150° C. and 5 torr (666 Pa).

A homogeneous, liquid organopolysiloxane composition, convertible to the solid state by ultraviolet radiation, was prepared by mixing 77.93 parts of the above vinyl-containing polydiorganosiloxane, 24.48 parts of a trimethylsiloxane-endblocked polymethylhydrogensiloxane having about 35 methylhydrogensiloxane units and 2.09 parts of benzophenone.

Aspirin was prepared for encapsulation by slurrying commercial tablets with water to dissolve water-soluble binders, filtering and drying the insoluble powder at 93° C. for 17 hours.

An emulsion of 33.3 g. of aspirin in 95 g. of the above homogeneous, convertible composition and 5 g. of a non-ionic surfactant was prepared using an Eppenbach mixer. The resulting emulsion was dispersed in 399 g. of water containing 1 g. of octylphenoxypolyethoxy(40)ethanol, using the quartz reaction vessel of Example 1. The uniformly stirred dispersions of discrete entities was irradiated for 130 minutes. The resulting microcapsules were filtered, washed and dried. Microscopic examination of the 1 to 2 mm microcapsules showed crystalline aspirin dispersed throughout the solid organopolysiloxane.

EXAMPLE 13

This example shows the rate of formation of solid microspheres as a function of the organopolysiloxane viscosity and the mol ratio of silicon-bonded hydrogen to silicon-bonded vinyl.

One hundred grams of the homogeneous, convertible composition of Example 12 was dispersed in 394 g. of water containing 6 g. of a 30 percent aqueous solution of sodium lauryl sulfate, using the quartz reaction tube of Example 1. This homogeneous convertible composition had a molar ratio of silicon-bonded hydrogen radicals to silicon-bonded vinyl radicals of 4:1. The stirred dispersion was irradiated until well-formed microspheres were obtained. The resulting microspheres were filtered, washed and dried as in the above examples.

This example was repeated with two other homogeneous, convertible compositions, identical to the above composition except that the vinyl-containing polydiorganosiloxane had viscosities of 5.5 and 8.9 Pa.s respectively, instead of 1.22 Pa.s.

The above example using the vinyl-containing polydiorganosiloxane having a viscosity of 8.9 Pa.s was repeated twice except that the molar ratio of silicon-bonded hydrogen to silicon-bonded vinyl was 10:1 to 1:1 respectively, instead of 4:1.

In each of the above experiments the irradiation times for the onset and completion of microsphere formation were noted and the size distribution of microparticles was measured. The results are summarized in the Table and show that the size of microspheres varies directly and the rate of formation of microspheres varies inversely with the viscosity of the vinyl-containing polydiorganosiloxane. Microsphere formation rate seems to be slightly favored by an $SiH/SiCH=CH_2$ molar ratio of 4:1 rather than 1:1 or 10:1.

TABLE

| Viscosity of Vinyl-containing Fluid (Pa·s) | $SiH/SiCH=CH_2$ Ratio | Irradiation Time To Microsphere Formation | | Microsphere Size (mm) |
|---|---|---|---|---|
| | | Onset (min.) | Complete (min.) | |
| 1.22 | 4:1 | 30–45 | 60 | 0.5–1.0 |
| 5.5 | 4:1 | 15–30 | 30–45 | 1.3–2.5 |
| 8.9 | 4:1 | 15 | 30 | 1.2–2.5 |
| 8.9 | 1:1 | 15–30 | 45–60 | 1.3–1.6 |
| 8.9 | 10:1 | 30 | 45–60 | 1.1–1.4 |

EXAMPLE 14

This example shows the preparation of microspheres of solid organopolysiloxne and their use as filler particles in a silicone rubber.

One hundred grams of the convertible composition of Example 12 was dispersed in 194 g. of water containing 6 g. of 30 percent aqueous solution lauryl sulfate (Duponol ® WAQ). using an Eppenbach laboratory mixer. The resulting emulsion was then diluted with an additional 200 g. of water and the resulting emulsion was irradiated using the quartz reaction vessel of Example 1. During the one hour of irradiation the temperature of the emulsion rose from 26° to approximately 34° C. The cured microspheres were isolated by pressure filtration and were washed with two portions of water. Microscopic examination showed the microspheres to have an average diameter of approximately 0.02 mm.

Two 100 g.-portions of a peroxide-curable silicon rubber stock were milled with 1 g. and 3 g., respectively, of the microspheres of this Example. The resulting filled rubber stocks, as well as the base stock, were cured and their durometers and break-moduli (ratio of tensile strength in p.s.i. to elongation in percent at break) were measured. The durometer of each sample was approximately 69, whereas the break-moduli were 4.52, 4.42 and 4.11 for the cured rubber containing 0 percent, 1 percent and 3 percent of microspheres, respectively.

I claim:

1. A process for preparing microspheres of solid organopolysiloxane, said process comprising
   (I) preparing a dispersion of discrete entities in a fluid continuous phase by dispersing, in the continuous phase fluid, a liquid organopolysiloxane composition, convertible by ultraviolet radiation to the solid state, said fluid continuous phase being transparent to ultraviolet radiation and said liquid organopolysiloxane composition being insoluble in the fluid continuous phase and consisting essentially of
      (a) an organopolysiloxane wherein an average of at least two of the organic radicals per molecule are silicon-bonded olefinic radicals selected from the group consisting of vinyl and butenylene and
      (b) a hydrogen-containing organopolysiloxane, free of aliphatic unsaturation, wherein the average molecule contains at least two hydrogen radicals selected from the group consisting of silicon-bonded hydrogen and mercaptoalkyl hydrogen, at least one of (a) and (b) having an average of more than two of said olefinic radicals and said hydrogen radicals, respectively, per molecule, and
   (II) exposing the dispersion of (I) to ultraviolet radiation until the liquid organopolysiloxane composition is converted to the solid state.

2. A process for preparing microcapsules consisting essentially of an internal material dispersed throughout a solid organopolysiloxane, said process comprising
   (I) preparing a dispersion of discrete entities in a fluid continuous phase by dispersing or dissolving the internal material in a liquid organopolysiloxane composition, convertible by ultraviolet radiation to the solid state, and dispersing the resulting dispersion or solution in the continuous phase fluid, said fluid continuous phase being transparent to ultraviolet radiation and said liquid organopolysiloxane composition being insoluble in the fluid continuous phase and consisting essentially of
      (a) an organopolysiloxane wherein an average of at least two of the organic radicals per molecule are silicon-bonded olefinic radicals selected from the group consisting of vinyl and butenylene and
      (b) a hydrogen-containing organopolysiloxane, free of aliphatic unsaturation, wherein the average molecule contains at least two hydrogen radicals selected from the group consisting of silicon-bonded hydrogen and mercaptoalkyl hydrogen, at least one of (a) and (b) having an average of more than two of said olefinic radicals and said hydrogen radicals, respectively, per molecule, and
   (II) exposing the dispersion of (I) to ultraviolet radiation until the liquid organopolysiloxane composition is converted to the solid state.

3. A process for preparing microcapsules consisting essentially of an internal material localized as a core in a solid organopolysiloxane, said process comprising
   (I) preparing a dispersion of discrete entities in a fluid continuous phase by dispersing the internal material in the continuous phase fluid and simultaneously or subsequently codispersing therewith a liquid organopolysiloxane composition, said fluid continuous phase being transparent to ultraviolet radiation and said liquid organopolysiloxane composition being insoluble in the fluid continuous phase and consisting essentially of
      (a) an organopolysiloxane wherein an average of at least two of the organic radicals per molecule are silicon-bonded olefinic radicals selected from the group consisting of vinyl and butenylene and
      (b) a hydrogen-containing organopolysiloxane, free of aliphatic unsaturation, wherein the average molecule contains at least two hydrogen radicals selected from the group consisting of silicon-bonded hydrogen and mercaptoalkyl hydrogen, at least one of (a) and (b) having an average of more than two of said olefinic radicals and said hydrogen radicals, respectively, per molecule, and
   (II) exposing the dispersion of (I) to ultraviolet radiation until the liquid organopolysiloxane composition is converted to the solid state.

4. A process according to claims 1, 2 or 3 wherein the liquid organopolysiloxane composition, convertible by ultraviolet radiation to the solid state, further contains a photosensitizing amount of a photosensitizer.

5. A process according to claim 4 wherein the fluid continuous phase is water comprising a dispersion-stabilizing amount of an oil-in-water surfactant.

6. A process according to claim 5 wherein the liquid organopolysiloxane composition consists essentially of a homogeneous mixture of
   (a) a triorganosiloxane-endblocked polydiorganosiloxane fluid having a viscosity of from 0.5 to 50 pascal-seconds at 25° C. and containing up to 10 mol percent methylvinylsiloxane units and at least 90 mol percent dimethylsiloxane units,
   (b) a triorganosiloxane-endblocked polymethylhydrogensiloxane having approximately 35 silicon atoms, and
   (c) a photosensitizing amount of benzophenone, the amounts of (a) and (b) being sufficient to provide a mol ratio of silicon-bonded hydrogen radicals to silicon-bonded vinyl radicals of from 1.0 to 10.0.

7. A process according to claim 5 wherein the liquid organopolysiloxane composition consists essentially of a homogeneous mixture of
   (a) an organopolysiloxane selected from the group consisting of cyclopolymethylvinylsiloxanes having from 3 to 10 silicon atoms and 1,1'-oxy-bis(1-methyl-1-silacyclopentene), (b) a triorganosiloxane-endblocked polydiorganosiloxane fluid having a viscosity of from 0.5 to 50 pascal-seconds at 25° C. and containing up to 10 mol percent methyl-3-mercaptopropylsiloxane units and at least 90 mol percent dimethylsiloxane units, and (c) a photosensitizing amount of benzophenone, the amounts of (a) and (b) being sufficient to provide a mol ratio of mercaptopropyl radicals to olefinic radicals of from 0.5 to 5.0.

8. A process according to claims 2 or 3 wherein the internal material is a medicament.

9. A process according to claim 8 wherein the medicament is aspirin.

10. A process according to claims 2 or 3 wherein the internal material is an enzyme.

11. A process according to claim 10 wherein the enzyme is urease.

12. A process according to claims 2 or 3 wherein the internal material is a biocide.

13. A process according to claim 12 wherein the biocide is 2,4-dichlorophenoxyacetic acid.

14. A process according to claim 12 wherein the biocide is 3,3-dimethyl-1-(methylthio)-2-butanone-O-{(methylamino)-carboxyl}oxime.

* * * * *

UNITED STATES PATENT AND TRADEMARK OFFICE
CERTIFICATE OF CORRECTION

PATENT NO. : 4,370,160
DATED : January 25, 1983
INVENTOR(S) : Maris J. Ziemelis

It is certified that error appears in the above-identified patent and that said Letters Patent is hereby corrected as shown below:

In column 2, line 1, "ether" should read -- ester --.

In column 3, line 28, "radiaton" should read -- radiation --.

In column 5, line 35, "$HCF_2$" should read -- $HCF_3$ --.

In column 5, line 38, "compoent" should read -- component --.

In column 17, line 11, "silicon" should read -- silicone --.

In column 17, line 21, "I claim:" should read
-- That which is claimed is: --.

Signed and Sealed this

Eleventh Day of December 1984

[SEAL]

Attest:

GERALD J. MOSSINGHOFF

Attesting Officer            Commissioner of Patents and Trademarks